United States Patent [19]
Carlson et al.

[11] Patent Number: 5,750,578
[45] Date of Patent: May 12, 1998

[54] USE OF BETULIN AND ANALOGS THEREOF TO TREAT HERPESVIRUS INFECTION

[75] Inventors: Robert M. Carlson; Pavel A. Krasutsky; M. Reza-Ul Karim, all of Duluth, Minn.

[73] Assignee: Regents of The University of Minnesota, Minneapolis, Minn.

[21] Appl. No.: 798,900

[22] Filed: Feb. 11, 1997

[51] Int. Cl.$^6$ .......................... A01N 27/00; A01N 31/00; A61K 39/245
[52] U.S. Cl. ............................ 514/766; 514/934
[58] Field of Search .................... 514/766, 934

[56] References Cited

PUBLICATIONS

Challand, R., et al., (eds.), "Herpes Viruses", Chapter 6, In: *Antiviral Chemotherapy, Biochemical & Medicinal Chemistry Series*, Spectrum & University Science Books, Sausalito, CA, pp. 54–67 (1996).
Arbesfeld, D.M., et al., "Cutaneous Herpes Simplex Virus Infections", *Am. Family Physician*, 43, 1655–1664, (1991).
Bean, B., "Acyclovir in the treatment of herpesvirus infections", *Postgrad. Med.*, 73, 297–303, (1983).
Chatis, P.A., et al., "Analysis of the Thymidine kinase gene from clinically isolated acyclovir–resistant herpes simplex viruses", *Virol.*, 180, 793–797, (1991).
Haase, A.T., "Methods in viral pathogenesis: tissues, organs and animals", *Virol. Pathologenesis*, N. Nathanson, ed., Lippincott–Raven publishers, Hagerstown, MD, 465–506, (1996).
Hayek, E.W., et al., "A bicentennial of betulin", *Phytochemistry*, 28, 2229–2242, (1989).
Konoshima, T., et al., "Studies on inhibitors of skin–tumor promotion, I. inhibitory effects of Triterpenes from *Euptelea polyandra* on epstein–barr virus activation", *J. of Natural Products*, 50, 1167–1170, (1987).
Pisha, E., et al., "Discovery of betulinic acid as a selective inhiibitor of human melanoma that functions by induction of apoptosis", *Nature Med.*, 1, 1046–1051, (1995).
Roizman, B., et al., "An inquiry into the mechanisms of herpes simplex virus latency", *Ann. Rev. of Microbiology*, 41, 543–571, (1987).
Roizman, B., et al., "Herpes simplex viruses and their replication", *Virol.*, Raven Press, NY (2nd ed.), 1795–1841, (1990).
Alarcon et al. Antiviral Research 4: 231–243, 1984.
Fujioka et al. CA 120: 289424v, J. Nat. Prod. 57(2): 243–247, 1994.
Platanov et al. CA 123: 334728x, Khim:–Farm Zh. 29(2): 42–46, 1995.
Tan et al. CA 117: 124048a, Biochem. Biophys. Res. Commun. 185(1): 370–378, 1992.
Alarcon et al. CA 102: 39536, Antiviral Research, 4(5): 231–244, 1984.

*Primary Examiner*—Gary L. Kunz
*Attorney, Agent, or Firm*—Schwegman, Lundberg, Woessner & Kluth, P.A.

[57] ABSTRACT

A therapeutic method is provided for treating a mammal afflicted with a herpesvirus infection comprising administering an effective amount of betulin or a derivative thereof.

11 Claims, No Drawings

USE OF BETULIN AND ANALOGS THEREOF TO TREAT HERPESVIRUS INFECTION

BACKGROUND OF THE INVENTION

The herpes simplex viruses (HSV) are a group of about 100 different double-stranded DNA animal viruses. At least seven are known to be pathogenic to humans and are known as human herpesviruses or HHV. HHV include herpes simplex virus type 1 and type 2 (HSV-1 and HSV-2), varicella zoster virus (VSV or HHV3, which causes chickenpox), cytomegalovirus (CMV), human herpesvirus type 6 and type 7 (HHV-6 and HHV-7) and Epstein-Barr virus (EBV or HHV4 which causes infectious mononucleosis). Infections by these viruses are among the most common and easily transmitted viral infections, afflicting greater than one million individuals each year in the United States. The hallmark of herpes virus infections is latency. The site of latency is the dorsal root ganglia or the sacral ganglia. Here the virus remains latent and can be reactivated under various conditions of stress. See, for example, B. Roizman et al., *Am. Rev. Microbiol.*, 41, 543 (1987); B. Roizman et al., "Herpes Simplex and Their Replication", B. Fields, ed., *Virology*, Raven Press, NY (2d ed., 1990) at pp. 1795–1841; A. H. Haase et al., *Viral Pathogenesis*, N. Nathanson, ed., Lippincott-Raven (1996) at pp. 465–506.

HSV-1 mainly affects areas above the waist and is most common in children between the ages of one and five. HSV-2 is primarily a sexually transmitted virus affecting the genital areas, sacrum and buttocks. These two types can infect any mucutaneous surface or visceral site and produce clinically indistinguishable lesions. The degree of infection greatly varies from patient to patient, however, those with T-cell defects experience more frequent and severe HSV infections (D. M. Arbesfeld et al., *Am. Family Physician*, 43, 1655 (1991)).

Numerous treatments for HSV infections have been tried and none have been entirely satisfactory. Chemotherapy (topical or systemic) for HSV infection has included the use of idoxuridine, trifluorothymidine, adenine arabinoside (ara-A), acyclovir, bromovinyl deoxyuridine, foscarnet, and other acyclic nucleoside analogues. Among all the anti-HSV agents, acyclovir (ACV) was the first genuinely selective agent. It profoundly affects viral DNA polymerase function through obligatory chain termination and competitive inhibition. See B. Beam. *Postgrad. Med.*, 77, 297 (1983). The poor absorption rate and pharmacokinetics of acyclovir have been overcome to some extent by the use of prodrugs like valaciclovir and penciclovir in treating infected individuals. However, many HSV-1 and HSV-2 strains have produced mutants that are resistant to ACV. Also, drugs such as ACV require the virus to be actively multiplying and are not active when the virus is latent. The greatest difficulty in finding antiviral compounds is due to the requirement that the active compound must act on virus within a host cell without causing damage to the host cell (A. Chatos et al., *Virol*, 180, 793 (1991)).

There is an increasing need for antiviral and antibacterial agents, because of therapeutic complications due to the emergence of new bacteria and viruses, and mutations of the old viral and bacterial species.

SUMMARY OF THE INVENTION

The present invention provides a therapeutic method for the treatment of herpesvirus infection comprising administering to a mammal, such as a human, afflicted with a herpesvirus infection, an effective anti-viral amount of a compound of formula (I):

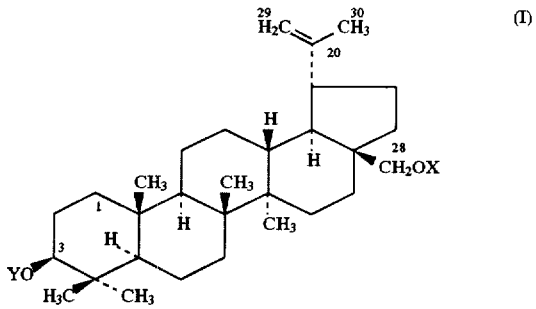

wherein X and Y are individually H, $O\!=\!P(OH)_2$, $O\!=\!P(OH)_2OP(O)(OH)$—, $(C_1\!-\!C_5)$alkanoyl, $Si(R)_3$ wherein each R is H, phenyl or $(C_1\!-\!C_6)$alkyl, $(C\!=\!O)N(R)_2$, benzyl, benzoyl, tetrahydropyran-2-yl, 1-[$(C_1\!-\!C_4)$alkoxy]$(C_1\!-\!C_4)$alkyl, a glycoside or a pharmaceutically acceptable salt thereof.

Preferably, at least one of X or Y is H or acetyl, most preferably both are H. The compound of formula (I) wherein both X and Y are H is betulin (lup-20(29)-ene-3, 28-diol).

The compounds of formula (I) may be administered as pharmaceutical compositions, locally or systemically, and are effective to treat (block or inhibit) herpesvirus infections, including active or latent infections. Susceptible herpesvirus infections include HSV-1, HSV-2, V2V, CMV, HHV-6, HHV-7 and HHV4 (Epstein-Barr virus) infections. They are particular effective against HSV-1 and HSV-2.

The invention also provides a method for isolating betulin comprising extracting a betulin source such as birch bark with chloroform at elevated (i.e., reflux) temperatures to yield a solution of betulin in chloroform, passing the betulin solution through a bed of silica gel to yield a betulin chrloroform eluate, and recovering the betulin from the eluate, i.e., by cooling the chloroform eluate and isolating the betulin by filtration, centrifugation, and the like.

DETAILED DESCRIPTION OF THE INVENTION

Betulin (lup-20(29)-ene-3β, 28-diol) is commercially available from the Sigma Chemical Co., St. Louis, Mo. inter alia and is described, along with the diacetate (X=Y=acetyl) in Merck 1212, *The Merck Index* (11th ed., 1989). See also, J. Simonsen et al., *The Terpenes*, Vol. IV, Cambridge U. Press (1957) at pages 187–328.

The mono- or diphosphate can be prepared as disclosed in Vince et al. (U.S. Pat. No. 5,175,292), employing appropriate protecting groups. The X and Y groups enumerated above are within the general class of "removable hydroxyl protecting groups", and can be prepared and removed by methods available to the art, including (a) reaction with silyl chlorides in the presence of organic amines, (b) reaction with (alkenyl)alkyl ethers under acid catalysis, (c) reaction with aroyl or alkanoyl anhydrides and organic bases, (d) reaction with benzoyl chloride and base, (e) reaction of the chloroformates with substituted amines to yield urethanes or with alcohols to yield carbonates, and the like.

Glycosides are formed by reacting mono-, di- and polysaccharides with 1-2 hydroxyl groups of the compound of formula (I), including glucose, glucuronic acid, mannose, galactose, sorbase, ribose, maltose, sucrose, modified cellulosics, dextrans, modified starches and the like. These derivatives can advantageously exhibit improved water solubility over betulin itself. See, *Remington's Pharmaceu-*

*tical Sciences*, A. R. Gennaro, ed., Mack Pub. Co. (18th ed., 1990) at pages 384–386.

Pharmaceutically acceptable salts include nontoxic amine salts and alkali metal salts of phosphates and nontoxic inorganic and organic acid addition salts of amines, such as the citrate, malonate, malate, tartarate, hydrochloride, sulfate, bicarbonate, and carbonate salts.

The compounds of formula (I) can be formulated as pharmaceutical compositions and administered to a mammalian host, such as a human patient afflicted with herpesvirus infection, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusable solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. The liquid compositions can also be employed as eyedrops, mouth washes, douches, etc. Antibacterial presaturated wipes are disclosed by Anderson (U.S. Pat. No. 4,896,768).

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Other examples of useful dermatological compositions which can be used to deliver the compounds of formula (I) to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

The invention will be further described by reference to the following detailed examples.

EXAMPLE 1

Betulin Extraction and Purification

Silica (60–100 mesh) (0.3 kg) and 1.0 kg of coarsely ground dry birch bark (Minnesota paper birch) was successively loaded into a Soxhlet apparatus. The lower silica layer is separated from the birch bark with a paper filter. The extractor is supplied with a heated 4 liter Erlenmeyer flask and two doubled-jacked condensers.

After 15 hours of extraction with 2.0 l. of refluxing chloroform, the yellow chloroform solution is cooled to ambient temperature for 4 hours and then the crystals are isolated by filtration. The resulting white crystalline material was recrystallized from 0.7 l. of chloroform (80–110 g, 8%–11% yield of >97% pure betulin is isolated, m.p., 256–257° C.).

For biological studies, the betulin was further recrystallized from isopropanol (yield 60–65%, m.p. 260–261° C.).

EXAMPLE 2

Pharmacological Studies

A. Materials and methods:

1. Cells:

Human epithelial type 2 (HEp2), African green monkey kidney (Vero) and human neuroblastoma (SK-N-MC) cells were purchased from American Type Culture Collection (ATCC-Rockville, Md.). These cells were grown at 37° C. in the presence of 5% carbon dioxide tension in minimal essential medium (MEM-Eagle) containing 0.1 mM of non-essential amino acids, and Earl's BSS 90% supplemented with 5% Newborn Calf Serum (NCS) and 1% penicillin/streptomycine sulfate. For SK-N-MC cells, 1.0 mM sodium pyruvate, and 10% NCS was used. The stock cells were prepared and stored at −80° C. in 5% dimethyl sulfoxide (DMSO).

2. Virus:

Two different HSV-1 and HSV-2 strains were used: HSV-1 (KOS), HSV-2 (MS). Also, HSV-1 (patent strain) and HSV-2 (patent strain) were purchased from ATCC and propagated in HEp2 cell monolayers. Virus stocks were prepared by adsorbing 1 ml of virus suspension containing $1 \times 10^5$ virus particles for one hour in HEp2 cells at 37° C. in 5% carbon dioxide tension. This stock was incubated under similar conditions for 48 hours after adding 15 ml of MEM containing the usual supplements.

Infected cells were harvested and disrupted through three cycles of freezing and thawing. The contents in the flasks were pooled, and the supernatant virus particles were collected by centrifugation at 3000 rpm for 5 minutes. The virus suspension dispensed in 2.5 ml aliquot each and filtered using both microtitration and plaque counting methods.

HSV-1 and HSV-2 containing $5 \times 10^4$ PFU/ml and $5.25 \times 10^4$ PFU/ml respectively were stored at −80° C. until needed.

3. Betulin Solution:

A betulin solution containing 0.5 mg of betulin/1000 ml of water was filtered using a 0.22 mM pore size filter (Gelman) attached to a 35 ml volume syringe to remove bacteria and other larger organisms. This sterile sample was further diluted to 1:2, 1:4, and 1:8 using distilled, deionized sterile water.

4. Cytotoxicity Test:

The cytotoxic effect of betulin was observed by using a 24-well microtiter plate. Each well contained 1 ml of MEM with supplements containing 1200 HEp2, Vero or SK-N-MC cells. The plates were incubated for 48 hours at 37° C. in 5% carbon dioxide tension and followed by replacement of the medium with 1.0 ml of MEM with specific supplements.

A 1.0 ml of sterile betulin solution in duplicate at varying two-fold dilution were placed into labeled wells. No betulin solution was placed in the control wells containing a monolayer of cells. These microtiter plates were incubated at 37° C. and 5% carbon dioxide tension for 48 hours and rated as follows.

A value of plus 3 (+++) was given to wells with normal monolayer development similar to cell control. Similarly, a plus 2 (++) for 75% monolayer, a plus one (+) for 50% monolayer, and a plus minus (±) for 25% monolayer development. A minus rating means that most of the cells are abnormal, whereas a double minus (—) rating was given to wells containing all abnormal cells due to cytotoxic effect of betulin solution. Noncytotoxic dilutions and the highest dilution of betulin showing cytotoxicity, if any, were used in the protection tests.

5. Cell Protection Tests:

Healthy HEp2, Vero or SK-N-MC monolayers were overlaid with 0.1 ml virus suspension containing 10 virions (M.O.I. 10) of HSV-1 or HSV-2, and incubated at 37° C. and 5% carbon dioxide tension for one hour for the adsorption of virus to different cell monolayers. All wells containing virus-infected cells were overlaid in duplicate with 0.9 ml MEM each containing specific supplements for specific cell lines and 1.0 ml of specific betulin dilution. Four controls, betulin, acyclovir, cell control and virus control were used as comparison to the test wells. All microtiter test plates were incubated at 37° C. with 5% carbon dioxide atmosphere and observed twice daily for 72 hours.

A plus 3 (+++) was given to the wells in which betulin solutions protected the cells without any cytopathic effect as compared to cell and betulin control. A plus 2 (++) for cells in wells with 75% protection, a plus 1 (+) for 50% protection, a plus minus (±) for 25% protection, a minus (−) with very little protection and a double minus (—) was given to the wells in which the cells showed no protection with complete cytopathic effect.

B. Results:

1. Cytoxicity Tests:

The highest concentration of betulin (0.5 mg/l) and other two-fold dilutions did not show any cytotoxic effect compared to control. Similarly, no cytotoxic effect was observed for highest concentration of acyclovir (50 mg/l) and its two-fold serial dilution. All cell lines showed a similar effect.

2. Cell Protection Tests:

Of the three different cell lines infected with HSV-1 and HSV-2, betulin was found to be more effective against HSV-2 compared to HSV-1 (Tables 1, 2, 3, 4, 5, and 6). Highest concentration of betulin or acyclovir was used as controls.

*TABLE 1

Effectiveness of betulin against HSV-1 in HEp2 cells [mg/l]

| Betulin | | | | Controls | |
|---|---|---|---|---|---|
| 0.5 mg | 0.25 mg | 0.125 mg | 0.0625 mg | | |
| ++± | ++ | ± | — | Cell +++ | Cell +++ |
| ++± | +± | ± | — | Betulin +++ | Betulin +++ |

| Acyclovir | | | | | |
|---|---|---|---|---|---|
| 25 mg | 12.5 mg | 6.25 mg | 3.125 mg | | |
| ++± | ++ | — | — | Acyclovir +++ | Acyclovir +++ |
| ++± | ++ | — | — | Virus — | Virus — |

*TABLE 2

Effectiveness of betulin against HSV-2 in HEp2 cells

| Betulin | | | | Controls | |
|---|---|---|---|---|---|
| 0.5 mg | 0.25 mg | 0.125 mg | 0.0625 mg | | |
| +++ | ++± | + | — | Cell +++ | Cell +++ |
| +++ | ++± | + | — | Betulin +++ | Betulin +++ |

| Acyclovir | | | | | |
|---|---|---|---|---|---|
| 25 mg | 12.5 mg | 6.25 mg | 3.125 mg | | |
| ++± | ++ | — | — | Acyclovir +++ | Acyclovir +++ |
| ++± | ++ | — | — | Virus — | Virus — |

*TABLE 3

Effectiveness of betulin against HSV-1 in vero cells

| Betulin | | | | Controls | |
|---|---|---|---|---|---|
| 0.5 mg | 0.25 mg | 0.125 mg | 0.0625 mg | | |
| ++± | +± | ± | — | Cell +++ | Cell +++ |
| ++± | +± | — | — | Betulin +++ | Betulin +++ |

| Acyclovir | | | | | |
|---|---|---|---|---|---|
| 25 mg | 12.5 mg | 6.25 mg | 3.125 mg | | |
| ++± | ++ | — | — | Acyclovir +++ | Acyclovir +++ |
| ++± | ++ | — | — | Virus — | Virus — |

*TABLE 4

Effectiveness of betulin against HSV-2 in vero cells

| Betulin | | | | Controls | |
|---|---|---|---|---|---|
| 0.5 mg | 0.25 mg | 0.125 mg | 0.0625 mg | | |
| +++ | ++ | ± | — | Cell +++ | Cell +++ |
| +++ | ++ | ± | — | Betulin +++ | Betulin +++ |

| Acyclovir | | | | | |
|---|---|---|---|---|---|
| 25 mg | 12.5 mg | 6.25 mg | 3.125 mg | | |
| ++± | +± | — | — | Acyclovir +++ | Acyclovir +++ |
| ++± | +± | — | — | Virus — | Virus — |

*TABLE 5

Effectiveness of betulin against HSV-1 in SK-N-MC cells

| Betulin | | | | Controls | |
|---|---|---|---|---|---|
| 0.5 mg | 0.25 mg | 0.125 mg | 0.0625 mg | | |
| ++± | +± | ± | — | Cell +++ | Cell +++ |
| ++± | +± | ± | — | Betulin +++ | Betulin +++ |

| Acyclovir | | | | | |
|---|---|---|---|---|---|
| 25 mg | 12.5 mg | 6.25 mg | 3.125 mg | | |
| +++ | +± | — | — | Acyclovir +++ | Acyclovir +++ |
| ++± | +± | — | — | Virus — | Virus — |

*TABLE 6

Effectiveness of betulin against HSV-2 in SK-N-MC cells

| Betulin | | | | Controls | |
|---|---|---|---|---|---|
| 0.5 mg | 0.25 mg | 0.125 mg | 0.0625 mg | | |
| +++ | ++ | ± | — | Cell +++ | Cell +++ |
| ++± | ++ | ± | — | Betulin +++ | Betulin +++ |

| Acyclovir | | | | | |
|---|---|---|---|---|---|
| 25 mg | 12.5 mg | 6.25 mg | 3.125 mg | | |
| ++± | +± | ± | — | Acyclovir +++ | Acyclovir +++ |
| ++± | + | — | — | Virus — | Virus — |

*+++ → complete protection (100%)
++± → protection with a few infective sites
++ → 75% protection
+± → more than 50% protection
+ → 50% protection
± → 25% protection
— → <5% protection
— → 100% infection The results presented hereinabove indicate that the highest water-soluble concentration of betulin (05. mg/l) is not toxic to human epithelial cells, African green monkey kidney cells and human neuroblastoma cells. These cells were used as indicator cells to test the effectiveness of betulin as compared to acyclovir (ACV) against HSV-1 (KOS, patent)

and HSV-2 (MS, patent) infection. The results indicated that 0.5 mg/l of betulin is as effective as 25 mg/l of ACV in protecting three different types of indicator cell monolayers. Furthermore, it was observed that betulin is slightly more effective in protecting all three different cell lines against HSV-2 strains than HSV-1 strains. The virus did not spread from the infected cells even after 72 hours and resulted in the protection of over 75% of the cell lines.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method for treatment of a human afflicted with a herpesvirus infection comprising administering to said human an effective antiviral amount of a compound of formula (I):

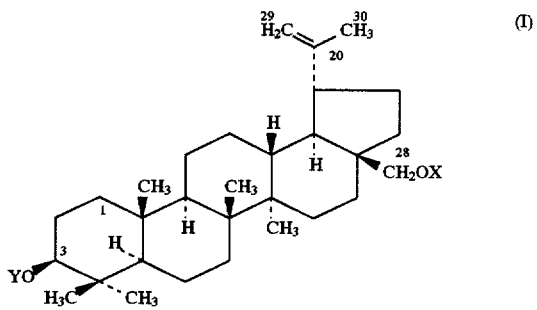

wherein X and Y are individually H, O=P(OH)$_2$, O=P(OH)$_2$, O=P(OH)$_2$OP(O)(OH)—, (C$_1$–C$_5$)alkanoyl, Si(R)$_3$, (C=O)N(R)$_2$, wherein each R is H, phenyl or (C$_1$–C$_6$)alkyl, benzyl, benzoyl, tetrahydropyran-2-yl, 1-[(C$_1$–C$_4$)alkoxy] (C$_1$–C$_4$)alkyl, a glycoside or a pharmaceutically acceptable salt thereof.

2. The method of claim 1 wherein X and Y are individually H or (C$_1$–C$_5$)alkanoyl.

3. The method of claim 1 wherein X and Y are individually O=P(O)$_2$.

4. The method of claim 1 wherein X and Y are individually a glycoside.

5. The method of claim 1 wherein X and Y are H.

6. The method of claim 1 wherein the compound of formula (I) is administered as a pharmaceutical composition in combination with a pharmaceutically acceptable vehicle.

7. The method of claim 6 wherein the composition is adapted for topical administration.

8. The method of claim 6 wherein the composition is adapted for oral administration.

9. The method of claim 6 wherein the composition is adapted for parenteral administration.

10. The method of claim 1 wherein the herpesvirus is HSV-1.

11. The method of claim 1 wherein the herpesvirus is HSV-2.

* * * * *